United States Patent [19]

Hirose et al.

[11] 4,055,639
[45] * Oct. 25, 1977

[54] DERIVATIVES OF N-(2,2-DICHLOROVINYL) SALICYLAMIDE AND USE THEREOF AS BACTERICIDES, FUNGICIDES AND ALGICIDES FOR INDUSTRY

[75] Inventors: Kiyonobu Hirose, Ageo; Shuichi Ishida, Omiya; Kaoru Omori, Okegawa, all of Japan

[73] Assignee: Nippon Kayaku Kabushiki Kaisha, Tokyo, Japan

[*] Notice: The portion of the term of this patent subsequent to Oct. 25, 1994, has been disclaimed.

[21] Appl. No.: 595,748

[22] Filed: July 14, 1975

[51] Int. Cl.$^2$ ............... A01N 9/24; A61L 31/60; C07C 69/86
[52] U.S. Cl. ............... 424/230; 260/559 S; 260/404; 260/404.5; 210/64; 560/142
[58] Field of Search ............... 424/230; 260/479 R, 260/480, 559 S

[56] References Cited

U.S. PATENT DOCUMENTS

| | | | |
|---|---|---|---|
| 2,895,992 | 7/1959 | Ohnacker et al. | 260/559 S |
| 2,923,737 | 2/1960 | Ruschig et al. | 260/559 S |
| 2,936,323 | 5/1960 | Eden | 260/558 |

OTHER PUBLICATIONS

Chemical Abstracts 75:139927z (1971).
Chemical Abstracts 78:42611r (1973).

*Primary Examiner*—Leonard Schenkman
*Attorney, Agent, or Firm*—Russell & Nields

[57] ABSTRACT

A new compound represented by the formula

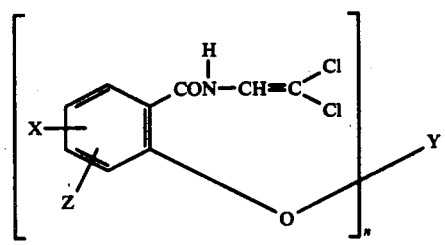

wherein X represents hydrogen atom, chlorine atom, bromine atom, methyl group or nitro group, Y represents hydrogen atom, methyl group, an alkylcarbonyl group where the alkyl group has from 1 to 12 carbon atoms and may be substituted by one or more halogen atoms, a lower alkoxy carbonyl group, a lower alkylamino carbonyl group or a metal atom of which the valence is 1 or 2, Z represents hydrogen atom or chlorine atom and $n$ represents 2 when Y represents a metal atom of which valence is 2 and $n$ represents 1 when Y represents said group or said atom except a metal atom of which valence is 2 but when X and Z represent hydrogen atom, Y does not represent hydrogen atom or a metal atom is employed to control the growth of bacteria, fungi and algae which propagate on industrial raw materials and products or in water in circulating water systems.

9 Claims, No Drawings

DERIVATIVES OF N-(2,2-DICHLOROVINYL) SALICYLAMIDE AND USE THEREOF AS BACTERICIDES, FUNGICIDES AND ALGICIDES FOR INDUSTRY

BACKGROUND OF THE INVENTION

The present invention relates to new derivatives of N-(2,2-dichlorovinyl)salicylamide and use thereof for controlling bacteria, fungi and algae which propagate on industrial raw materials, industrial products and in water in circulating water systems.

The bacteria and fungi on industrial raw materials and products degrade the quality of industrial raw materials and products and cause various other troubles. The damage is very serious. The algae which propagate on the bottom of ships cause the slowdown of speed of ships.

Bacteria, fungi and algae in water in circulating water systems produce mats of slime which restrict the flow of water and reduce the efficiency of heat exchange. They constitute a considerable problem.

Many compounds having bactericidal, fungicidal and algicidal activity are used for prevention of the damage caused by the bacteria, fungi or algae to industrial raw materials and products and the impediment caused by slime in circulating water systems. These compounds include, for example, organic mercury compouds, organic tin compounds, phenols having substituted halogen atoms, organic sulfur compounds, formalin, cresol and quaternary ammonium salts. These compounds, however, have various defects, for example, strong toxicity against humans and live-stock, pollution of environment, irritative or offensive odor, bad influence upon industrial raw materials and products and weak bactericidal, fungicidal activity.

SUMMARY OF THE INVENTION

It is, therefore, the object of the present invention to provide new compounds having bactericidal, fungicidal and algicidal activity against bacteria, fungi and algae which propagate on industrial raw materials and products and in water in circulating water systems, to provide methods for controlling such bacteria, fungi and algae and to provide compositions used for the methods.

The compounds of the present invention are represented by the formula:

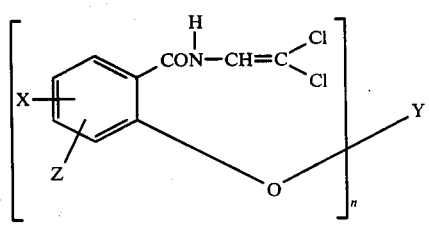

(1)

wherein X represents hydrogen atom, chlorine atom, bromine atom, methyl group or nitro group, Y represents hydrogen atom, methyl group, an alkylcarbonyl group where the alkyl group has from 1 to 12 carbon atoms and may be substituted by one or more halogen atoms, a lower alkoxy carbonyl group, a lower alkyl-amino carbonyl group or a metal atom of which the valence is 1 or 2, Z represents hydrogen atom or chlorine atom and $n$ represents 2 when Y represents a metal atom of which valence is 2 and $n$ represents 1 when Y represents said group or said atom except a metal atom of which valence is 2, but when X and Z represent hydrogen atom, Y does not represent hydrogen atom or a metal atom.

The methods of the present invention comprise applying to industrial raw materials, industrial products and water in circulating water systems an effective amount of one or more compounds of formula (1).

The bactericidal, fungicidal and algicidal compositions of the present invention comprise 99.5-5% by weight of a suitable adjuvant and 0.5-95% by weight of one or more compounds of formula (1).

The industrial raw materials and products include organic matter: for example, cellulosic material such as wood, wooden articles, paper, cotton, fibers, textiles and bamboo, petroleum products such as plastics, plastic articles, oils and paints and leathers; inorganic matter such as metal articles; and products consisting of organic and inorganic matter such as ships and sheds for animals.

The term "circular water systems" means a system in which water is used many times by cycling. Such circulating water systems include, for example, the water systems in cooling towers for air conditioning, swimming pools, cooling equipments for reactors and the paper manufacturing industry.

Suitable adjuvants of the composition of the present invention include, for example, carriers, extenders, emulsifying agents, wetting agents, fixing agents and surface active agents. The term "carrier" is used herein to mean a diluent or vehicle by which the active compound is brought into contact with bacteria, fungi and algae.

Solid carrier materials and liquid carrier materials are usually used as carriers in the present invention. Solid carrier materials include, for example, clay, kaolin, talc, diatomaceous-earth, silica and calcium carbonate. Liquid carrier materials include, for example, benzene, alcohol, acetone, xylene, methylnaphthalene, cyclohexanone, dimethylformamide, diethylsulfoxide, animal and vegetable oils, fatty acids and ester thereof and various surface active agents.

DESCRIPTION OF THE INVENTION

The compounds of the present invention have superior bactericidal, fungicidal and algicidal activity against bacteria, fungi and algae which propagate on industrial raw materials and industrial products and in water in circulating water systems and have no irritative or offensive odor and very low toxicity. The value of acute oral toxicity of the compound of the present invention against as mouse, which is represented by $LD_{50}$, is more than 1000 mg/kg. Accordingly, the compounds are safe to handle. Therefore, the compounds are used for controlling said bacteria, fungi and algae.

The preferred compounds are the compounds of formula (1) in which X represents hydrogen atom, chlorine atom, bromine atom or methyl group, Y represents methyl group, an alkylcarbonyl group where the alkyl group has from 1 to 3 carbon atoms and may be substituted by one or two chlorine atoms, a lower alkoxy carbonyl group where the lower alkoxy group has from 1 to 4 carbon atoms, methylamino carbonyl group, sodium atom, potassium atom, zinc atom or manganese atom, Z represents hydrogen atom or chlorine atom and $n$ represents 2 when Y represents a metal atom of which valence is 2 and $n$ represents 1 when Y represents said group or said atom except a metal atom of which valence is 2. The most preferred compounds are the compounds of the formula (1) in which X represents hydrogen atom or chlorine atom, Y represents sodium atom, methylcarbonyl group, ethylcarbonyl group or methoxy carbonyl group and $n$ represents 1. These compounds are, for example, sodium salts of N-(2',2'-dichlorovinyl)-5-chlorosalicylamide, O-acetyl-N-(2',2'-dichlorovinyl)-5-chlorosalicylamide, O-acetyl-N-(2',2'-dichlorovinyl) salicylamide and)-ethylcarbonyl-N-(2,2-dichlorovinyl)-salicylamide.

The compounds of the formula (1) of the present invention are prepared as follows:

The compound of the formula

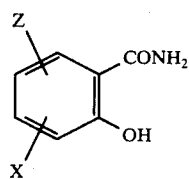

(II)

wherein X and Z are defined as above are condensed with chloral by a method similar to that shown in U.S. Pat. No. 2,936,323. The products of the condensation are compounds of the formula

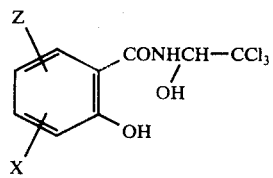

(III)

These compounds are reduced with a reductant such as zinc in a suitable solvent such as acetic acid, methanol or ethanol at a temperature between room temperature and 120° C.

Compounds of the formula

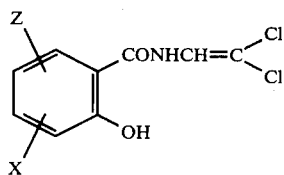

(IV)

are obtained by the said reduction. The compound of the formula (IV) is reacted with equivalent mole to 2 times mole of an alkyl halide, an acyl chloride, an alkoxycarbonyl chloride or an alkyl isocyanate in the presence of a suitable base such as trimethylamine and triethylamine in an inactive solvent at a temperature of 5° to 120° C to obtain the compound

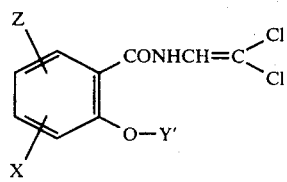

(V)

wherein Y' represents methyl group, an alkylcarbonyl group where the alkyl group has from 1 to 12 carbon atoms and may be substituted by one or more halogen atoms, a lower alkoxy carbonyl group, a lower alkyl amino carbonyl group, and X and Z are defined as above.

The alkyl halide is, for example, methyl iodide, ethyl iodide or propyl chlorine. The acyl chloride where alkyl group may be substituted halogen atoms is, for example, acetyl chloride, chloroacetylchloride, dichloroacetyl chloride, propionyl chloride, butyryl chloride, isobutyryl chloride or lauroyl chloride. The alkoxy carbonyl chloride is, for example, methyl chloroformate, ethyl chloroformate or propyl chloroformate. The alkyl isocyanate is, for example, methyl isocyanate or propyl isocyanate.

The compound of the formula (IV) is reacted with equivalent of an alkali metal hydroxide in water at room temperature to obtain the formula

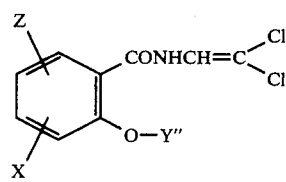

(VI)

wherein Y'' represents alkali metal such as sodium atom or potassium atom.

The alkali metal hydroxide is, for example, sodium hydroxide or potassium hydroxide.

The compound of the formula (IV) is reacted with equivalent of a metal halide except alkali metal halide, a metal acetate or a metal sulfate in the presence of alkali metal hydroxide such as sodium hydroxide or potassium hydroxide in water at room temperature to obtain the formula

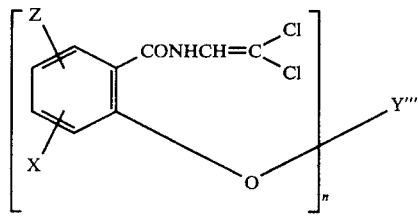

wherein Y''' represents metal atom except alkali metal atom and $n$ represents 1 or 2.

The metal halide is, for example, zinc chloride or manganous chloride. The metal acetate is, for example, zinc acetate or copper (II) acetate. The metal sulfate is, for example, copper sulfate.

In order to control the growth of said bacteria, fungi and algae with the compounds of the present invention, the compounds are applied to industrial raw materials, industrial products and said water.

The compounds, themselves, may be directly applied to said materials, products and water. However, in general, one or more of the compounds are mixed with suitable adjuvants and formed into bactericidal fungicidal and algicidal compositions such as emulsifiable concentrate, wettable powder, water soluble concentrate, oil soluble concentrate, dust, granules or pellets.

The bactericidal, fungicidal and algicidal composition which contains the compounds of the present invention comprises about 0.5 to 95, preferably, 2 to 70 weight percent of the compounds and about 99.5 to 5, preferably 98 to 30 weight percent of suitable adjuvants.

In the case of treatment of industrial raw materials or products such as wood, wooden articles, fibers, textiles, paper, leathers, inside of sheds for animals, etc., usually their surfaces are treated with 0.1–10 g/m² of the compound in the form of a composition by means of spraying, coating or infiltrating.

In the case of treatment of industrial raw materials or products such as paints, adhesives and pastes, etc., usually the compound in the form of a composition is added to them and mixed. The amount of the compound added is usually about 0.01 to 0.1 percent by weight.

The growth of bacteria, fungi and algae on the bottom of ships can be prevented by coating the bottom with the paint containing the compound.

In the case of treatment of water in circulating water systems, the active compound is added to the water and the amount of the active compound is usually about 2 to 50 ppm, preferably about 10 to 30 ppm.

EXAMPLE 1

Preparation of N-(2',2'-dichlorovinyl)-5-chlorosalicylamide (Compound No. 1)

Thirty (30) g (0.09 mol) of N-(1'-hydroxy-2',2',2'-trichloroethyl)-5-chlorosalicylamide were dissolved in 150 ml of acetic acid. Nine point two (9.2) g (0.14 mol) of zinc powder were added into the solution under stirring at the temperature from 20° to 40° C and the reaction was continued for 4 hours at the same temperature. The temperature was finally raised at 80° C and then excess zinc was removed by filtration. The filtrate was cooled to obtain 28 g of crystals of N-(2',2'-dichlorovinyl)-5-chlorosalicylamide was obtained. Melting point of it was 208°–210° C.

Elemental analysis for $C_9H_6Cl_3NO_2$:
Calculation: C, 40.56%; H, 2.27%; N, 5.26%. Found: C, 40.37%; H, 2.23%; N, 5.65%.

EXAMPLE 2

Preparation of O-acetyl-N-(2,2-dichlorovinyl) salicylamide (Compound No. 2)

One hundred and fifty (150) g (0.65 mol) of N-(2,2-dichlorovinyl) salicylamide was suspended into 450 ml of benzene. Two hundred (200) g (1.95 mol) of acetic anhydride was added into the suspension with stirring. After 10 g (0.13 mol) of pyridine was added dropwise to the solution at 30°–40° C, the mixture was refluxed for 5 hours. After cooling, the reaction mixture was washed with water and an aqueous solution of 5%-sodium hydrogen-carbonate, and again with water.

Then the reaction mixture was condenced under the reduced pressure to obtain a solid matter. The solid matter was recrystallized from cyclohexane. One hundred and seventy (170) g of O-acetyl-N-(2,2-dichlorovinyl) salicylamide, m.p. 91°–92° C, was obtained.

Elemental analysis for $C_{11}H_9Cl_2NO_3$: Calculation: C, 48.20%; H, 3.31%; N, 5.11%. Found: C, 48.30%; H, 3.06%; N, 5.08%.

EXAMPLE 3

Preparation of O-methoxycarbonyl-N-(2,2-dichlorovinyl) salicylamide (Compound No. 3)

Twenty (20) g (0.09 mol) of N-(2,2-dichlorovinyl) salicylamide were dissolved into 100 ml of benzene. Eight point one (8.1) g (0.09 mol) of methyl chloroformate were added to the solution with stirring. After 9 g (0.09 mol) of triethylamine were added dropwise under 10° C the mixture was reacted for 3 hours at the room temperature and refluxed for 30 minutes to complete the reaction. After cooling, the reaction mixture was washed with water, an aqueous solution of 5%-sodium hydrogencarbonate, and finally with water to obtain the neutral reaction mixture. The neutral reaction mixture was concentrated under reduced pressure to obtain a solid matter. The solid matter was recrystallized from methanol. Twenty two point five (22.5) g of O-(N'-methoxy carbamoyl)-N-(2,2-dichlorovinyl) salicylamide, m.p. 72°–73° C, was obtained.

Elemental analysis for $C_{11}H_9Cl_2NO_4$:
Calculation: C, 45.54%; H, 3.13%; N, 4.83%. Found: C, 45.30%; H, 3.10%; N, 4.61%.

EXAMPLE 4

Preparation of O-(N'-methylcarbamoyl)-N-(2,2-dichlorovinyl) salicylamide (Compound No. 4)

Twelve (12) g (0.05 mol) of N-(2,2-dichlorovinyl) salicylamide were dissolved in 100 ml of benzene and 4 g (0.07 mol) of methyl isocyanate were added with stirring at below 10° C. Six point six (6.6) g (0.07 mol) of triethylamine were added dropwise to the solution. The mixture was reacted for 3 hours at room temperature and refluxed for 30 minutes. The reaction mixture was cooled and washed with water, then an aqueous solution of 5%-sodium hydrocarbonate and finally water to obtain the neutral reaction mixture. The neutral reaction mixture was concentrated to obtain a solid matter under the reduced pressure. The solid matter was recrystallized from methanol. Thirteen point five (13.5) g of O-(N'-methylcarbamoyl)-N-(2,2-dichlorovinyl) salicylamide (m.p. 98°–101° C) were obtained.

Elemental analysis for $C_{11}H_{10}Cl_2N_2O_3$: Calculated: C, 45.70%; H, 3.49%; N, 9.69%. Found: C, 45.81%; H, 3.45%; N, 9.60%.

EXAMPLE 5

Preparation of O-acetyl-N-(2',2'-dichlorovinyl)-5-chlorosalicylamide (Compound No. 5)

Five (5) g (0.018 mol) of N-(2',2'-dichlorovinyl)-5-chlorosalicylamide were dissolved in 30 ml of benzene, and 2.2 g (0.022 mol) of acetic anhydride and a few drops of pyridine were added with stirring. The mixture was stirred for 4 hours at 50° C. The reaction mixture was washed with water, an aqueous solution of 5%-sodium hydrocarbonate and water, successively. The reaction mixture was concentrated under the reduced pressure to obtain a solid matter. The solid matter was recrystallized from benzene. Four (4) g of O-acetyl-N-(2',2'-dichlorovinyl)-5-chlorosalicylamide, m.p. 98°–100° C, were obtained.

Elemental anarysis for $C_{11}H_7Cl_3NO_3$: Calculation: C, 42.82%; H, 2.61%; N, 4.54%. Found: C, 42.65%; H, 2.70%; N, 4.41%.

EXAMPLE 6

The preparation of sodium salt of N-(2',2'-dichlorovinyl)-5-chlorosalicylamide (Compound No. 6)

Five (5) g (0.019 mol) of N-(2',2'-dichlorovinyl)-5-chlorosalicylamide were added under agitation to the aqueous solution wherein 0.7 g (0.019 mol) of 93%-sodium hydroxide were dissolved in 30 ml of water and then agitated at room temperature for 1 hour.

Water was evaporated under reduced pressure. The yields of sodium salt of N-(2',2'-dichlorovinyl)-5-chlorosalicylamide was 5.4. The sodium salt was pale light brown crystals and melting point of it was over 280° C.

Elemental analysis as $C_9H_5Cl_3NO_2Na_5$: Calculated: C, 37.47%; H, 1.75%; N, 4.86%. Found: C, 37.33%; H, 1.73%; N, 4.79%.

EXAMPLE 7

The compounds shown in Table 1 were prepared.

Table 1

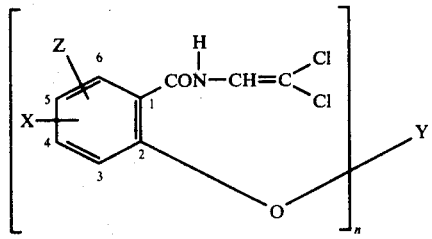

| Compound No. | X and position of | Y | Z | n | M.P. (° C) or $n_D^{25}$ | Appearance | Method of the preparation | A material compound corresponding to Y group |
|---|---|---|---|---|---|---|---|---|
| 7 | 5-Br | Na | H | 1 | Over 280 | Pale brown crystals | Similar method to Example 6 N-(2',2'-dichlorovinyl)-5-bromo-salicylamido was reacted with equivalent of $Zncl_2$ in the presence of NaOH in water at room temperature. | NaOH |
| 8 | 5-Br | Zn | H | 2 | " | White crystals | | $ZnCl_2$ |
| 9 | 5-Br | Cu (II) | H | 2 | " | Dark yellow green crystals | Similar method to the preparation of compound No. 8 | $CuSO_4$ |
| 10 | 5-Br | Mu (II) | H | 2 | " | Yellow grey crystals | " | $MnCl_2$ |
| 11 | 4-$CH_3$ | H | H | 1 | m.p. 189–191 | White crystals | Similar method to Example 1 | |
| 12 | 3-$CH_3$ | H | H | 1 | m.p. 78–82 | White crystals | " | |
| 13 | 5-Br | H | H | 1 | m.p. 204 | White crystals | " | |
| 14 | 3-$NO_2$ | H | H | 1 | m.p. 176–177 | Pale yellow crystals | Nitration of N-(2,2-dichlorovinyl) salicyl-amide with equivalent mole of nitric acid in the presence of acetic acid at room temperature. | |
| 15 | H | $C(O)C_2H_5$ | H | 1 | m.p. 37–38 | White crystals | Similar method to Example 2 | $ClC(O)C_2H_5$ |
| 16 | H | $C(O)C_3H_7(n)$ | H | 1 | m.p. 124–125 | White crystals | " | $ClC(O)C_3H_7(n)$ |
| 17 | H | $C(O)C_3H_7(i)$ | H | 1 | m.p. 122–124 | White crystals | " | $ClC(O)C_3H_7(i)$ |
| 18 | H | $C(O)C_{11}H_{23}(n)$ | H | 1 | m.p. 53–59 | White crystals | " | $ClC(O)C_{11}H_{23}(n)$ |
| 19 | H | $C(O)CH_2Cl$ | H | 1 | m.p. 93–95 | White crystals | Similar method to Example 2 | $ClC(O)CH_2Cl$ |
| 20 | H | $C(O)CHCl_2$ | H | 1 | m.p. 184–186 | White crystals | " | $ClC(O)CHCl_2$ |
| 21 | 5-Br | $C(O)CH_3$ | H | 1 | m.p. 133–134 | White crystals | Similar method to Example 5 | $ClC(O)CH_3$ |
| 22 | H | $C(O)OC_2H_5$ | H | 1 | m.p. 70–72 | White crystals | Similar method to Example 3 | $ClCOOC_2H_5$ |
| 23 | H | $C(O)OCH_2CH(CH_3)_2$ | H | 1 | $n_D^{25}$ 1.5409 | Transparet liquid | " | $ClCOOCH_2CH(CH_3)_2$ |
| 24 | H | $CH_3$ | H | 1 | m.p. | White | Alkylation of N-(2,2-dichlorovinyl) salicyl- | $CH_3I$ |

Table 1-continued

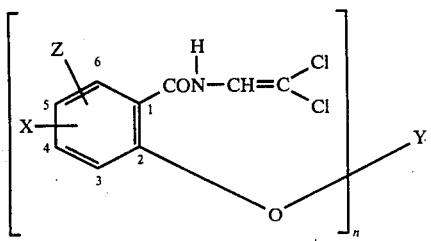

| Compound No. | X and position of | Y | Z | n | M.P. (° C) or $n_D^{25}$ | Appearance | Method of the preparation | A material compound corresponding to Y group |
|---|---|---|---|---|---|---|---|---|
| | | | | | 111–112 | crystals | amide with methyl iodide | |
| 25 | 5-Cl | K | H | 1 | m.p. over 280 | Pale Yellow crystals | Similar method to Example 6 | KOH |
| 26 | 3-Cl | H | 5-Cl | 1 | m.p. 173.5–174.0 | White crystals | Similar method to Example 1 | |
| 27 | 3-Cl | C(O)CH$_3$ | 5-Cl | 1 | m.p. 130–132 | White crystals | Similar method to Example 5 | ClC(O)CH$_3$ |
| 28 | 3-Cl | Na | 5-Cl | 1 | m.p. over 280 | Pale yellow crystals | Similar method to Example 6 | NaOH |
| 29 | 3-Cl | K | 5-Cl | 1 | m.p. over 280 | Pale yellow crystals | " | KOH |
| 30 | 3-NO$_2$ | C(O)CH$_3$ | H | 1 | m.p. 109–112 | Pale yellow crystals | Similar method to Example 5 | ClC(O)CH$_3$ |

EXAMPLE 8

An emulsifiable concentrate was prepared as follows:
Compound No. 1: 10 parts
Isophorone: 40 parts
Xylene: 31 parts
Dimethylformamide: 7 parts
Surface active agents: 12 parts The above ingredients were blended. An emulsifiable concentrate was obtained. Before application, the emulsifiable concentrate was diluted with water up to 400–2000 times and an emulsion was formed. Woods and fibers were soaked in the emulsion to control bacteria and fungi which propagate on them.

An emulsifiable concentrate containing compound No. 2, No. 5, No. 8, No. 10, No. 13, No. 15, No. 16, No. 19, No. 22 or No. 23 was prepared by the same method as mentioned above.

EXAMPLE 9

An oil soluble concentrate was prepared as follows:
Compound No. 15: 20 parts
Ethyl cellosolve: 40 parts
Dimethylformamide: 10 parts
Xylene: 30 parts The above ingredients were mixed. An oil soluble concentrate was obtained. In the form of the oil soluble concentrate, Compound No. 15 was added to paints or the cutting oil in an amount of 0.1%.

EXAMPLE 10

A wettable powder was prepared as follows:
Compound No. 5: 55 parts
Polyethyleneoxide: 3 parts
Ligninsulfonic acid: 5 parts
Diatom earth: 20 parts
Clay: 17 parts The above ingredients were blended. A wettable powder was obtained. Before application, the wettable powder was suspended in water. The resultant suspension was sprayed on the inside of sheds for animals by a sprayer to prevent the growth of fungi and bacteria in sheds for animals.

EXAMPLE 11

A water soluble concentrate was prepared as follows:
Compound No. 6: 10 parts
Ethyl cellosolve: 40 parts
Isophoron: 38 parts
Polyethyleneoxide: 10 parts
Alkylbenzenesulfonic acid: 2 parts The above ingredients were mixed. A water soluble concentrate was obtained. A water soluble concentrate containing Compound No. 1, No. 2, No. 5, No. 8, No. 16, No. 19 or No. 22 was prepared by the same method as mentioned above.

Before application, the concentrate was diluted 500–1000 times with water and sprayed on the inside of cotes to prevent the growth of bacteria and fungi.

The solution was added to water in circular water systems to inhibit the growth of slime. The concentration of Compound No. 6 in the water was 10–20 ppm.

An amount of 0.01–0.1% of Compound No. 6 as the solution was added to pastes or binding agents to prevent rottenness of them. Bacteria, fungi and slime were inhibited for a long time.

EXAMPLE 12

Bactericidal activity and fungicidal activity of the active compounds of the present invention were examined by [1] potato-dextrose agar dilution method, or [2] glucose bouillon medium dilution method. The results are shown in Table 2 below as the minimum inhibitory concentration (the minimum concentration of active compound found to produce 100% control of the test bacteria and fungi).

Table 2

| | Minimum inhibitory amount (mcg/ml) | | | | | |
|---|---|---|---|---|---|---|
| Method | (1) | | | (2) | | |
| | | | Bacteria and Fungi | | | |
| Active Compound No. | Aspergillus niger | Penicillium citrinum | Cladosporium harbarum | Bacillus subtilis | Staphylococcus aureus | Escherichia coli |
| 1 | 10 | 10 | 5 | 5 | 5 | 60 |
| 2 | 10 | 10 | 5 | 2.5 | 5 | 40 |
| 3 | 10 | 20 | 10 | 10 | 10 | 60 |
| 4 | 20 | 10 | 5 | 10 | 10 | 60 |
| 5 | 2.5 | 2.5 | 2.5 | 1.3 | 1.3 | 10 |
| 6 | 10 | 5 | 5 | 2.5 | 2.5 | 40 |
| 8 | 20 | 20 | 10 | 5 | 5 | 60 |
| 10 | 20 | 20 | 10 | 5 | 10 | 60 |
| 12 | 20 | 20 | 20 | 10 | 10 | 80 |
| 13 | 20 | 10 | 10 | 5 | 5 | 60 |
| 14 | 10 | 10 | 10 | 5 | 5 | 60 |
| 15 | 10 | 10 | 5 | 2.5 | 5 | 40 |
| 16 | 10 | 10 | 5 | 5 | 10 | 60 |
| 17 | 10 | 10 | 10 | 5 | 5 | 40 |
| 19 | 10 | 10 | 5 | 5 | 5 | 40 |
| 20 | 10 | 10 | 10 | 5 | 10 | 60 |
| 22 | 10 | 10 | 10 | 5 | 2.5 | 40 |
| 23 | 10 | 10 | 10 | 5 | 5 | 40 |
| 24 | 20 | 20 | 10 | 10 | 10 | 60 |
| 26 | 10 | 10 | 5 | 5 | 5 | 40 |
| 27 | 10 | 5 | 5 | 2.5 | 2.5 | 40 |

EXAMPLE 13

The emulsifiable concentrates which were prepared by Example 8 were diluted with water 400 times and 800 times to form emulstions.

The square plates of beach of which a side was 5 cm long and thickness was 5 mm were dipped into the emulsion for 2 minutes and dried for 24 hours at room temperature.

The square plates were placed on the surface of agar plates. The suspensions which contained spores of Aspergillus niger, Penicillium citrinum, Cladosporium harbarum and chaetomium globusum were respectively sprayed on the agar plates and the square plates.

The test fungi were cultivated in the incubator at the humidity of 95% and the temperature of 28° C for 2 weeks.

The results are shown in Table 3. The degree of growth inhibition is defined in term of the following numerical ratings.

Table 3

| | Degree of growth inhibition | |
|---|---|---|
| Concentrate of active compound Compound | 0.025 % | 0.0125 % |
| 1 | 3 | 2 |
| 2 | 3 | 3 |
| 5 | 5 | 5 |
| 8 | 3 | 2 |
| 10 | 3 | 2 |
| 13 | 3 | 3 |
| 15 | 3 | 3 |
| 16 | 3 | 3 |
| 19 | 3 | 2 |
| 22 | 3 | 2 |
| 23 | 3 | 2 |
| No treatment | 1 | 1 |

3 : 100% control of the test organism.
2 : The part in which the test organisms propagated is less than one third of the surface of the test plate.
1 : The part in which the test organisms propagated is more than one third of the surface of the test plate.

EXAMPLE 14

The emulsifiable concentrates which were prepared by Example 8 were diluted with water 100 times to form an emulsion.

A cloth of cotton was soaked into each emulsion for 2 minutes. The clothes were dried at room temperature and cut into a square of which a side was 1 cm long. Each kind of test bacteria and fungi was inoculated, separately, on plates of potato-agar and one square cloth was placed on each of such plates. Test bacteria and fungi were cultivated at 28° C for 4 days. The width of the region of growth-inhibition which was formed a circumference of the cloth was measured. The results are shown in Table 4.

Table 4

| | The width of the region of growth-inhibition(mm) | | | |
|---|---|---|---|---|
| | Fungi | | Bacteria | |
| Compound No. | Aspergillus niger | Penicillium citrinum | Bacillus subtilis | Staphylococcus oureus |
| 1 | 5 | 5 | 9 | 10 |
| 2 | 5 | 7 | 9 | 7 |
| 5 | 10 | 10 | 12 | 11 |
| 8 | 6 | 5 | 6 | 6 |
| 15 | 6 | 6 | 9 | 7 |
| 19 | 6 | 7 | 7 | 6 |
| 22 | 5 | 6 | 8 | 7 |
| No treated | 0 | 0 | 0 | 0 |

EXAMPLE 15

Zero point zero two (0.02) part of active compounds in the form of 10% water soluble concentrate which was prepared by Example 11 was added into 100 parts of Waxman's liquid medium. Pieces of wood and iron (hereafter referred to as the slime test boards) were soaked into the Waxman's liquid medium. The bacteria which were gathered from circular water system were inoculated upon the Waxman's liquid medim and incubated at 27°-34° C by shaking culture for 2 days. The degree of propagation of the bacteria on the slime test boards was examined.

The growth-inhibiting activity of active compounds against the fungi and the green algae was also examined by the same method as mentioned above.

The results are shown in Table 5.

The degree of propagation of the bacteria, fungi or green algae on the slime test boards is difined in term of the following symbols.

Table 5

| Compound | Degree of propagation | | |
|---|---|---|---|
| No. | Bacteria | Fungi | Green algae |
| 1 | − | − | − |
| 2 | − | − | − |
| 5 | − | − | − |
| 6 | − | − | − |
| 8 | + | + | + |
| 15 | − | − | − |
| 16 | + | − | − |
| 19 | − | − | − |
| 22 | − | + | + |
| No treatment | ++++ | ++++ | ++++ |

− : no propagation
+ : the area of propagation is 1–25% on the slime test boards.
++ : the area of propagation is 26–50% on the slime test boards.
+++ : the area of propagation is 51–75% on the slime test boards.
++++ : the area of propagation is 76–100% on the slime test boards.

We claim:
1. A compound represented by the formula

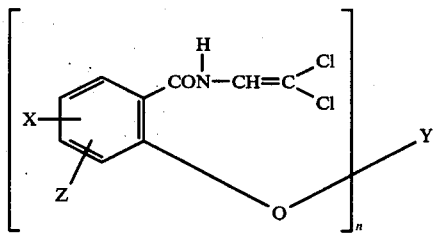

wherein X represents hydrogen atom, chlorine atom, bromine atom, methyl group or nitro group, Y represents hydrogen atom, methyl group, an alkylcarbonyl group where the alkyl group has from 1 to 12 carbon atoms and may be substituted by one or more halogen atoms, a lower alkoxy carbonyl group, a lower alkylamino carbonyl group or a metal atom of which valence is 1 or 2, Z represents hydrogen atom or chlorine atom and $n$ represents 2 when Y represents a metal atom of which valence is 2 and $n$ represents 1 when Y does not represent a metal atom of which valence is 2, but when X and Z represent hydrogen atom, Y does not represent hydrogen atom or a metal atom.

2. A compound according to claim 1 wherein X represents hydrogen atom, chlorine atom, bromine atom or methyl group, Y represents methyl group, an alkylcarbonyl group where the alkyl group has from 1 to 3 carbon atoms and may be substituted by one or two chlorine atoms, a lower alkoxy carbonyl group where the lower alkoxy group has from 1 to 4 carbon atoms, methylamino carbonyl group, sodium atom, pottassium atom, zinc atom or manganese atom and $n$ represents 2 when Y represents a metal atom of which valence is 2 and $n$ represents 1 when Y does not represent a metal atom of which valence is 2.

3. A compound according to claim 2 wherein X represents hydrogen atom or chlorine atom, Y represents sodium atom.

4. A method for killing bacteria, fungi and algae comprising applying to industrial raw materials, industrial products and water in circular water systems an effective amount of one or more compounds of the formula

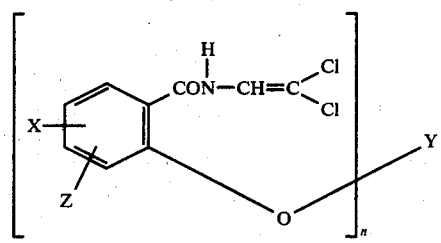

wherein X represents hydrogen atom, chlorine atom, bromine atom, methyl group or nitro group, Y represents hydrogen atom, methyl group, an alkylcarbonyl group where the alkyl group has from 1 to 12 carbon atoms and may be substituted by one or more halogen atoms, a lower alkoxycarbonyl group, a lower alkylamino carbonyl group or a metal atom of which valence is 1 or 2, Z represents hydrogen atom or chlorine atom and $n$ represents 2 when Y represents a metal atom of which valence is 2 and $n$ represents 1 when Y does not represent a metal atom of which valence is 2, but when X and Z represent hydrogen atom, Y does not represent hydrogen atom or a metal atom.

5. A method for killing bacteria, fungi and algae according to claim 4 wherein X represents hydrogen atom, chlorine atom, bromine atom, or methyl group, Y represents methyl group an alkylcarbonyl group where the alkyl group has from 1 to 3 carbon atoms and may be substituted by one or two chlorine atoms, a lower alkoxycarbonyl group where the lower alkoxy group has from 1 to 4 carbon atoms, methylamino carbonyl group, sodium atom, pottassium atom, zinc atom or manganese atom and $n$ represents 2 when Y represents a metal atom of which valence is 2 and $n$ represents 1 when Y does not represent a metal atom of which valence is 2.

6. A method for killing bacteria, fungi and algae according to claim 5 wherein X represents hydrogen atom or chlorine atom, Y represents sodium atom, methylcarbonyl group or ethylcarbonyl group and $n$ represents 1.

7. A bactericidal, fungicidal and algicidal composition comprising 99.5–5% by weight of a suitable adjuvant and 0.5–95% by weight of one or more compounds of general formula

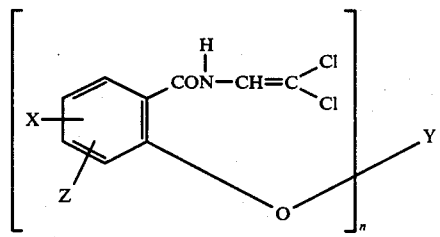

wherein X represents hydrogen atom, chlorine atom, bromine atom, methyl group or nitro group, Y represents hydrogen atom, methyl group, an alkylcarbonyl group where the alkyl group has from 1 to 12 carbon atoms and may be substituted by one or more halogen atoms, a lower alkoxy carbonyl group, a lower alkylamino carbonyl group or a metal atom of which valence is 1 or 2, Z represents hydrogen atom or chlorine atom and $n$ represents 2 when Y represents a metal atom of which valence is 2 and $n$ represents 1 when Y does not represent a metal atom of which valence is 2, but when X and Z represent hydrogen atom, Y does not represent hydrogen atom or a metal atom.

8. A bactericidal, fungicial and algicidal composition according to claim 7 wherein X represents hydrogen atom, chlorine atom, bromine atom or methyl group, Y represents methyl group, an alkylcarbonyl group where the alkyl group has from 1 to 3 carbon atoms and may be substituted by one or two chlorine atoms, a lower alkoxy carbonyl group where the lower alkoxy group has from 1 to 4 carbon atoms, methylamino carbonyl group, sodium atom, pottassium atom, zinc atom or manganese atom and $n$ represents 2 when Y represents a metal atom of which valence is 2 and $n$ represents 1 when Y does not represent a metal atom of which valence is 2.

9. A bactericidal, fungicidal and algicidal composition according to claim 8 wherein Y represents sodium atom, methylcarbonyl group or ethylcarbonyl group and $n$ represents 1.

* * * * *